(12) United States Patent
Thompson

(10) Patent No.: US 10,959,834 B2
(45) Date of Patent: Mar. 30, 2021

(54) STRUCTURES AND METHODS FOR TEAR SHAPING FOR REFRACTIVE CORRECTION

(71) Applicant: Vance M. Thompson, Sioux Falls, SD (US)

(72) Inventor: Vance M. Thompson, Sioux Falls, SD (US)

(*) Notice: Subject to any disclaimer, the term of this patent is extended or adjusted under 35 U.S.C. 154(b) by 0 days.

(21) Appl. No.: 16/373,751

(22) Filed: Apr. 3, 2019

(65) Prior Publication Data

US 2020/0085565 A1 Mar. 19, 2020

Related U.S. Application Data

(63) Continuation of application No. 16/134,426, filed on Sep. 18, 2018.

(51) Int. Cl.
| | | |
|---|---|---|
| *A61F 2/14* | (2006.01) | |
| *A61F 9/00* | (2006.01) | |
| *G02C 7/04* | (2006.01) | |
| *G02C 7/02* | (2006.01) | |
| *A61F 2/48* | (2006.01) | |

(52) U.S. Cl.
CPC ............ *A61F 2/14* (2013.01); *A61F 2/142* (2013.01); *A61F 2/145* (2013.01); *A61F 2/1451* (2015.04); *A61F 2/1453* (2015.04); *A61F 2/15* (2015.04); *A61F 9/00* (2013.01); *G02C 7/022* (2013.01); *G02C 7/049* (2013.01); *A61F 2002/482* (2013.01); *A61F 2210/009* (2013.01); *A61F 2230/0006* (2013.01); *A61F 2230/0008* (2013.01); *A61F 2250/0056* (2013.01); *A61F 2250/0091* (2013.01)

(58) Field of Classification Search
CPC ........ A61F 2/142; A61F 2/145; A61F 2/1451; A61F 2/1453; A61F 2/14; A61F 2/15; A61F 9/00; G02C 7/022; G02C 7/049
See application file for complete search history.

(56) References Cited

U.S. PATENT DOCUMENTS

| | | |
|---|---|---|
| 4,235,985 A | 11/1980 | Tanaka et al. |
| 4,464,026 A | 8/1984 | Comparetto |
| 4,744,647 A | 5/1988 | Meshel et al. |
| 5,114,686 A | 5/1992 | Gillespie |

(Continued)

FOREIGN PATENT DOCUMENTS

| | | |
|---|---|---|
| KR | 10-2005-0052442 | 6/2005 |
| WO | WO 95/08135 | 3/1995 |

(Continued)

OTHER PUBLICATIONS

Application and File History for U.S. Appl. No. 16/134,426, filed Sep. 18, 2018. Inventor: Vance M. Thompson.

(Continued)

*Primary Examiner* — William H Matthews
(74) *Attorney, Agent, or Firm* — Patterson Thuente Pedersen, P.A.

(57) ABSTRACT

A tear shaping structure or structures that shape a tear film of an eye thereby enabling a desired refractive effect. The tear shaping structure includes a supporting structure supporting a plurality of capillary action members, the capillary action members being spaced apart and arranged in such a way as to create a desired refractive lens effect by shaping the tear film of an eye.

13 Claims, 6 Drawing Sheets

(56) References Cited

U.S. PATENT DOCUMENTS

| | | |
|---|---|---|
| 5,245,367 A | 9/1993 | Miller et al. |
| 5,396,583 A | 3/1995 | Chen et al. |
| 5,580,498 A | 12/1996 | Sugiyama et al. |
| 5,658,602 A | 8/1997 | Martin et al. |
| 5,757,458 A | 5/1998 | Miller et al. |
| 5,804,107 A | 9/1998 | Martin et al. |
| 5,953,098 A | 9/1999 | Lieberman et al. |
| 5,980,040 A | 11/1999 | Xu et al. |
| 6,039,899 A | 3/2000 | Martin et al. |
| 6,312,393 B1 | 11/2001 | Abreu |
| 6,794,456 B2 | 9/2004 | Grobe, III |
| 6,880,932 B2 | 4/2005 | Doshi |
| 7,691,916 B2 | 4/2010 | McCabe et al. |
| 8,450,387 B2 | 5/2013 | McCabe et al. |
| 8,480,227 B2 | 7/2013 | Qiu et al. |
| 8,827,447 B2 | 9/2014 | Awasthi et al. |
| 8,911,083 B2 | 12/2014 | Brent |
| 9,310,627 B2 | 4/2016 | Havenstrite et al. |
| 2003/0105521 A1 | 6/2003 | Perez |
| 2003/0125498 A1 | 7/2003 | McCabe et al. |
| 2003/0162862 A1 | 8/2003 | McCabe et al. |
| 2005/0046794 A1 | 3/2005 | Silvestrini |
| 2006/0007391 A1 | 1/2006 | McCabe et al. |
| 2007/0016292 A1 | 1/2007 | Perez |
| 2007/0229757 A1 | 10/2007 | McCabe et al. |
| 2008/0002149 A1 | 1/2008 | Fritsch |
| 2008/0015282 A1 | 1/2008 | McCabe et al. |
| 2008/0024717 A1 | 1/2008 | Kim |
| 2008/0182956 A1 | 7/2008 | Stanbro et al. |
| 2008/0316424 A1 | 12/2008 | McCabe et al. |
| 2010/0072642 A1 | 3/2010 | Broad et al. |
| 2010/0084775 A1 | 4/2010 | McCabe et al. |
| 2010/0133710 A1 | 6/2010 | McCabe et al. |
| 2011/0116034 A1 | 5/2011 | Goto et al. |
| 2011/0146206 A1 | 6/2011 | Stanbro et al. |
| 2011/0273663 A1* | 11/2011 | Pugh ............... G02C 7/04 351/159.74 |
| 2012/0193822 A1 | 8/2012 | McCabe et al. |
| 2013/0053953 A1 | 2/2013 | Silvestrini |
| 2013/0225715 A1 | 8/2013 | McCabe et al. |
| 2013/0237631 A1 | 9/2013 | McCabe et al. |
| 2013/0265507 A1 | 10/2013 | Ford et al. |
| 2014/0192327 A1 | 7/2014 | Sindt et al. |
| 2014/0377327 A1 | 12/2014 | Davis et al. |
| 2015/0041736 A1 | 2/2015 | McCabe et al. |
| 2015/0092156 A1 | 4/2015 | Qiu et al. |
| 2015/0305929 A1 | 10/2015 | Goldberg et al. |
| 2016/0054589 A1 | 2/2016 | Otts et al. |
| 2016/0056508 A1 | 2/2016 | Flitsch et al. |
| 2016/0223836 A1 | 8/2016 | Havenstrite et al. |
| 2016/0266405 A1* | 9/2016 | Thompson ............. G02C 7/047 |
| 2017/0082869 A1 | 3/2017 | Sindt et al. |
| 2017/0087014 A1 | 3/2017 | Potter, Jr. et al. |
| 2017/0160432 A1 | 6/2017 | Havenstrite et al. |
| 2017/0242271 A1 | 8/2017 | Pugh et al. |
| 2018/0001581 A1 | 1/2018 | Patel et al. |
| 2018/0120589 A1 | 5/2018 | Thompson |

FOREIGN PATENT DOCUMENTS

| | | |
|---|---|---|
| WO | WO 97/34185 | 9/1997 |
| WO | WO 02/06883 A2 | 1/2002 |
| WO | WO 03/022321 A2 | 3/2003 |
| WO | WO 2009/069264 | 4/2011 |
| WO | WO 2012/051223 A2 | 4/2012 |
| WO | WO 2014/012016 A1 | 1/2014 |
| WO | WO 2014/074477 A2 | 5/2014 |
| WO | WO 2014//100836 A2 | 6/2014 |
| WO | WO 2014/205252 A2 | 12/2014 |
| WO | WO 2015/073758 A1 | 5/2015 |
| WO | WO 2016/014403 A1 | 1/2016 |
| WO | WO 2016/090863 A1 | 6/2016 |
| WO | WO 2016/115369 A1 | 7/2016 |
| WO | WO 2016/145204 A1 | 9/2016 |
| WO | WO 2017/037611 A1 | 3/2017 |
| WO | WO 2017/053673 A1 | 3/2017 |
| WO | WO 2017/096087 A1 | 6/2017 |
| WO | WO 2017/103793 A1 | 6/2017 |

OTHER PUBLICATIONS

PCT International Search Report for International Application No. PCT/US2019/051622, dated Jan. 3, 2020, 15 pages.

* cited by examiner

STRUCTURES AND METHODS FOR TEAR SHAPING FOR REFRACTIVE CORRECTION

RELATED APPLICATION

This application is a continuation of application Ser. No. 16/134,426, filed Sep. 18, 2018, which is hereby fully incorporated herein by reference.

TECHNICAL FIELD

Embodiments of the invention relate to refractive vision correction. More particularly they relate to refractive vision correction by shaping the tear film.

BACKGROUND

The tear film covers the anterior structures of the eye and is generally considered to be multilayered in structure. From the corneal surface outward the tear film includes a mucin layer, an aqueous layer and a lipid layer. The mucin layer overlies the surface of the cornea and the conjunctiva and serves to provide an interface between the corneal epithelium and the conjunctival epithelium and the further layers of the tear film. Without the mucin layer the corneal epithelium is generally considered to be hydrophobic because it contains considerable amounts of lipid. Overlying the mucin layer is the aqueous layer consisting largely of water and a small amount of salt and various other trace chemicals. Overlying the aqueous layer is the lipid layer formed of secretions of the meibomian glands and other lipid secreting glands located in and around the eyelids. The tear film protects the tissues of the corneal epithelium from drying and also fills in or bridges minor gaps or irregularities in the corneal epithelium to provide a smooth refractive surface interface between the front of the eye and the ambient atmosphere. In a sense, the functioning of contact lenses is based on shaping the tear film in that the contact lens both rests upon and is immersed in or covered by the tear film. Thus, the anterior most refractive interface between the air and the eye is actually formed by the tear film rather than the cornea itself.

The interface between the tear film and the atmosphere represents the most powerful optical focusing interface in the eye. The tear film interface with the atmosphere accounts for approximately two thirds of the focusing power the eye. This focusing power is approximately 43 diopters. Because the focusing power at the tear film interface is so large, small changes in the tear film can have a large effect on refraction and clarity of focusing.

Contact lenses can be considered to shape the tear film directly. That is, the contact lens places a new optical surface in front of the corneal epithelium and the tear film flowing over or overlying the anterior surface of contact lens assumes the general shape of the anterior surface of the contact lens in situ.

Contact lenses have been in existence for many decades. Early contact lenses were made of glass or rigid plastic such as polymethylmethacrylate (PMMA). Early contact lens designs were quite large and are referred to as scleral or haptic lens. Scleral or haptic contact lens designs cover the cornea completely as well as covering a large portion of the conjunctiva or sclera of the eye. The sclera is the structural white of the eyeball while the conjunctiva is a transparent tissue which overlies the sclera as well as covering the backside of the eye lids. Early contact lens designs were made of rigid, largely oxygen impermeable polymers as discussed above or a very few of glass. Because corneal physiology was poorly understood at the time these lenses were made, they often cause great discomfort and negative effect on corneal health.

As time went by, in the 1950's, hard contact lenses made of polymethylmethacrylate became much smaller having a diameter significantly smaller than that of the cornea. Hard corneal contact lenses were more comfortable and less physiological damaging than scleral or haptic lenses, but only marginally so. Hard contact lenses still significantly deprived the cornea of a necessary oxygen supply from atmospheric oxygen to maintain good corneal health and were difficult to adapt to. In the 1970s, so called soft corneal contact lenses became available. Soft contact lenses generally are larger than hard corneal contact lenses having a diameter approximating that of the cornea, somewhat larger than the cornea or somewhat smaller than the cornea. Soft contact lenses are generally made of hydrophilic polymers, such as polyhydroxy ethylmethacrylate (poly HEMA), that absorb substantial amounts of water, saline solution or the tear film. Soft contact lenses also provided improved comfort due to their permeability to oxygen and due to their more flexible nature. Later still, so called gas-permeable contact lenses became available. Gas permeable rigid contact lenses are similar in size and structure to hard corneal contact lenses but are made of rigid oxygen permeable polymers that allow oxygen and other gases to pass through the material of the contact lens to provide improved corneal health. Generally, rigid contact lenses provide sharper vision than soft contact lenses though this is not universally true.

Hard contact lenses as well as scleral or haptic contact lenses were sometimes fenestrated. That is, tiny holes were drilled or otherwise formed through the rigid contact lens material in an effort to improve tear exchange under the contact lens or to provide a greater availability of oxygen and other gases through the oxygen impermeable contact lens. Fenestration was generally not a very successful technique. Fenestrations, however, were uniformly tiny holes generally much smaller than one millimeter in diameter. Occasionally multiple fenestrations were present. Fenestrations were generally provided in an effort to benefit the health of the cornea.

All contact lenses known to the applicant are formed of substantially solid optical material.

Numerous possible complications are known to exist with use of contact lenses on the cornea even though modern contact lenses cause fewer complications than contact lenses of decades ago. The presence of contact lenses can lead to stasis and entrapment of the tear film which can lead to an accumulation of corneal epithelial waste products in the entrapped tear film. Corneal epithelial waste products, in high enough concentrations, can be toxic to the cells of the corneal epithelium. Mechanical interaction between the posterior surface of the contact lens and the corneal epithelium can lead to abrasion or distortion. Entrapment of solid objects, however tiny, between the posterior surface of the contact lens and the anterior corneal epithelium can also lead to corneal epithelial abrasion. Under some circumstances, the reduction of oxygen or other gases in available to the corneal epithelium by having the barrier of the contact lens between the corneal epithelium and the atmosphere can lead to health complications for the corneal epithelium as well.

Most forms of refractive surgery involve altering the structure of the cornea to alter the shape of the cornea and thus to alter the shape of the overlying tear film. Despite considerable advances in refractive surgery it is not an option that is available to all people due to various factors.

Many potential refractive surgery patients are not good subjects for refractive surgery for a variety of reasons and pre-existing conditions. Accordingly, many individuals still utilize glasses or contact lenses for refractive correction and there is still a need for nonsurgical refractive correction techniques.

There is still room for improvement in the arts of refractive correction by shaping the tear film.

SUMMARY

Embodiments of the invention are expected to solve many of the above problems.

Embodiments of the invention include a variety of structures that shape the tear film indirectly. As discussed above conventional contact lenses shape the fear tear film directly by providing a surface over which the tear film spreads evenly thus altering the shape of the tear film-atmosphere interface.

Indirect shaping of the tear film refers to the effect of physical structures on the fear film that is adjacent to the physical structure or structures. Accordingly, indirect shaping of the tear film takes place largely in portions of the tear film that do not overlie the tear shaping structures themselves. Instead, the indirectly shaped portions of the tear film are generally located in spaces between the tear shaping structures. Thus, indirect tear shaping is expected to provide benefits to corneal health by minimizing the amount of material separating the atmosphere in the tear film from the corneal epithelium. Capillary action based tear shaping structures according to example embodiments the invention are unlike conventional contact lenses in that they do not necessarily have an optical focusing effect when they are independent of the tear film or another liquid. At least the forces of capillary action and surface tension of tears contribute to the indirect tear shaping focusing effect according to embodiments of the invention. Capillary action based tear shaping structures may, according to one example embodiment of the invention, take the form of particulate structures instilled in the tears. Such particulate structures may vary in shape, size and density in order to achieve a desired tear shaping effect. Capillary action based tear shaping structures may also include an interior space or cavity in which tear film may reside to cause or enhance the indirect tear shaping effect.

The application of capillary action based tear shaping structures is expected to assist in retaining tears overlying the cornea and also is expected to assist tear exchange and gas exchange at the corneal epithelium. It is also expected that the application of capillary action based tear shaping structures may contribute to the maintenance or improvement of tear film health.

A liquid will form a concave meniscus when molecules of the liquid have greater attraction to a solid surface or structure than the liquid's molecules have to each other. Another way of stating this is that a concave meniscus will form when adhesion of the liquid to the solid is greater than cohesion of the liquid to itself. In the case of a liquid that is largely water, such as tears of the eye, this occurs because the polarity of the molecules that make up the solid may be greater than the polarity of the water molecules themselves. Liquids containing nonpolar molecules are more likely to form a convex meniscus.

Polarity of the water molecule and hydrogen bonding between water molecules contributes to the cohesion of liquid water and to the surface tension of liquid water. Surface tension of liquid water exists because the water molecules at the surface of the water are more strongly attracted to each other than they are to the surrounding air.

According to example embodiments of the invention, tear film shaping structures are utilized to create localized concave menisci and thus a negative optical power to correct for myopia. According to further example embodiments tear film shaping structures are utilized to create localized convex menisci and thus a positive refractive power to correct for hyperopia or presbyopia.

Embodiments of the invention include tear film shaping structures having a meshwork structure that utilize capillary attraction and adhesion between the tear film and the tear film shaping structure to shape the tear film supported by the meshwork thus altering the refractive effect of the tear film. According to embodiments of the invention, the meshwork structure provides a sufficient platform for the tear film to be shaped like a contact lens shapes the tear film through the capillary attraction and adhesion. It is expected that the closer fibers or structural elements of the structure are the more tear film there will be present thus creating a greater plus power to correct hyperopia. It is also expected that with a greater distance between fibers of the meshwork structure a lesser thickness of tear film will be present centrally and a more negative power to correct myopia will be available. According to example embodiments of the invention, the distance separating fiber structures or structural members within the meshwork lens may be greater at the center and less in the periphery which is expected to provide a myopic correcting lens. Alternatively, the meshwork structure may be more closely spaced a centrally and more distantly spaced peripherally to create a plus powered or hyperopic correcting lens.

According to one example embodiment, the meshwork structure is made up of a grid of fibers oriented substantially perpendicular to one another. In this context, substantially perpendicular means within 15° of perpendicular.

According to another example embodiment, the meshwork structure is made up of radially oriented and circumferentially oriented fibers. According to this example embodiment, the radially oriented fibers may vary from perfectly radially oriented by 15° or more to accomplish the desired tear shaping for refractive outcome. The center point from which the radially oriented fibers emanate may be located at a geometrical center of the meshwork or off-center. Further, according to this example embodiment, the circumferentially oriented or elliptical fibers may describe a true circle or may describe oval or racetrack shapes or other more irregular shapes to create a desired refractive outcome. For example, oval or racetrack shapes may assist in providing correction for astigmatism by shaping the tear film unequally along different meridians.

According to another embodiment of the invention, concentric ring structures are thinner and/or separated by a greater distance centrally and are thicker and/or closer together peripherally. It is expected that this will create a minus lens effect for correction of myopia. According to another embodiment of the invention, concentric ring structures are thicker and/or closer together centrally and thinner and/or farther apart preferably which is expected to create a plus lens effect to assist in correcting for hyperopia.

In addition to fibers oriented in a grid, radially and circumferentially oriented or in other orientations the fibers may further support other structures. For example, the fibers may support or include spheres, cubes, tetrahedra or octahedra or other polyhedral shaped structures as well as a ring shaped structures to assist in shaping the tear film. Shapes may also include the five Platonic solids as well as other three-dimensional structures. The shaped structures may be located at intersections of the fibers or at other locations along the fibers.

According to further example embodiments of the invention, the fibers or rods that form the mesh may vary in thickness, spacing or cross-sectional shape to assist in shaping the tear film. The mesh may also be formed by perforating a solid structure with a multitude of openings. The openings may be circular, square, rectangular, polygonal or any other shape. Such perforations may be accomplished by mechanical machining techniques, laser machining techniques or chemically based techniques. Chemically based techniques may include etching, plating or electroplating for example. Structures including such perforations may also be manufactured by additive manufacturing techniques such as three-dimensional printing.

According to another example embodiment, the mesh portion of the structure may be surrounded by a solid supporting perimeter portion.

According to example embodiments of the invention, it is expected that the spacing between structural members of the mesh portion will provide a different refractive correction depending upon spacing of the structural members. It is expected that greater spacing between the structural members will lead to a more negative refractive correction while closer spacing between the structural members will lead to a more positive refractive correction on the basis of capillary attraction or adhesion between the tear film and the structural members of the mesh portion.

According to another example embodiment, the structural members of the mesh may include surface features such as nodules or bumps at a microscopic or nano structural size level in order to further assist in shaping the tear film as desired.

According to another example embodiment, wettability of the structural members of the mesh may be adjusted by selection of materials and surface texture or surface features to facilitate achieving a desired refractive correction. Materials may be selected for example, based on the polarity of their constituent molecules and/or the relative electronegativity of the atoms in the material.

The mesh may be formed of a durable material or may be formed of a bioabsorbable or bio degradable material. For example, dissolvable structures of the mesh can be formed of collagen.

According to another example embodiment of the invention, the structural members may be separate individual structural members that are positioned relative to one another by attractive and repulsive forces.

According to another example embodiment of the invention, the structural members may be applied as a liquid suspension which is instilled into the tears such that individual structural members may position themselves relative to one another by attractive and repulsive forces. The structural members may be supported in a sol or gel suspension. The structural members may also be partially cross-linked or interlinked while in the suspension and further organized once instilled in the tear film.

The structural members, according to an example embodiment of the invention, may be organized by electrostatic forces, magnetic forces, intermolecular forces, and/or various repulsive and/or attractive forces. According to example embodiments of the invention structural members may vary in size and configuration. A suspension may include structural members of a single size and configuration or of several sizes and configurations. According to example embodiments of the invention, the mesh or structural refractive members may be organized to provide correction for myopia, presbyopia, hyperopia, astigmatism, and prismatic correction.

According to example embodiments of the invention, the structural members may include microscopic structural members, nanostructural members or nano-robots.

According to another example embodiment, meshwork structural members may be configured to provide correction for myopia, hyperopia, astigmatism, presbyopia and other refractive errors. According to another example embodiment meshwork structural members may be configured to improve image quality by reducing higher-order aberrations or spherical aberration of the eye or by providing compensation for corneal irregularities that exist due to disease or injury.

According to other example embodiments of the invention meshwork structural members may be formed of materials utilized in the manufacture of soft or rigid contact lenses. They may also be formed of materials that are intended for long-term use or materials that are biodegradable or bioabsorbable or configured for disposable use.

According to other example embodiments of the invention, meshwork structures may include various sizes of particles that are grouped or utilized for support to influence tear film shape to correct village vision including nanostructures and nanotechnology.

According to another example embodiment of the invention, capillary attraction, surface tension and other forces are used to shape the tear film by application of the meshwork structures. Accordingly, the meshwork or tear shaping structure provides a sufficient structural platform for the tear film to be shaped in a similar way to that like a contact lens shapes the tear film but based on capillary attraction, adhesion, surface tension and other forces.

For example, according to another embodiment a large number of tiny spheres or objects of various shapes and sizes can be instilled in the tear film. The effect of these multiple objects is expected to be to change the shape of the tear film between the multiple objects thereby creating a desired refractive effect at the interface between the tear film and the atmosphere. For example, it is expected that the tear film may be caused to take on a concave shape between adjacent objects in the tear film thus creating a negative lens effect to assist in correction of myopia. Depending upon the size and shape or the combination of objects of varying sizes and shapes it is expected that a toric focusing effect may be accomplished to assist in correction of astigmatism, that a plus lens effect may be achieved to assist in correction of hyperopia in that a multifocal effect may be obtained to assist in the correction of presbyopia. It is further expected that various shapes of objects may be used to define the distance between the objects to achieve a desired tear film shaping to provide refractive correction.

According to a further example embodiment the invention a large number of tiny rings or hollow cylindrical objects may be instilled into the tear film. It is expected that the effect of these rings or hollow cylindrical objects will be to alter the curvature of the overlying tear film such that incoming light rays made the divergent by a plus or minus lens effect created between the particles and/or that incoming light rays may be convert by a plus lens effect created over are within the open part of the rings or hollow cylindrical objects in the tear film.

It is expected that by varying the size and shape of the rings or hollow cylindrical objects in the tear film that many desired refractive effects may be achieved. For example, refractive effects to assist in correction of myopia, hyperopia, astigmatism, presbyopia and prismatic effect may be achieved.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

DETAILED DESCRIPTION

Figure 1:
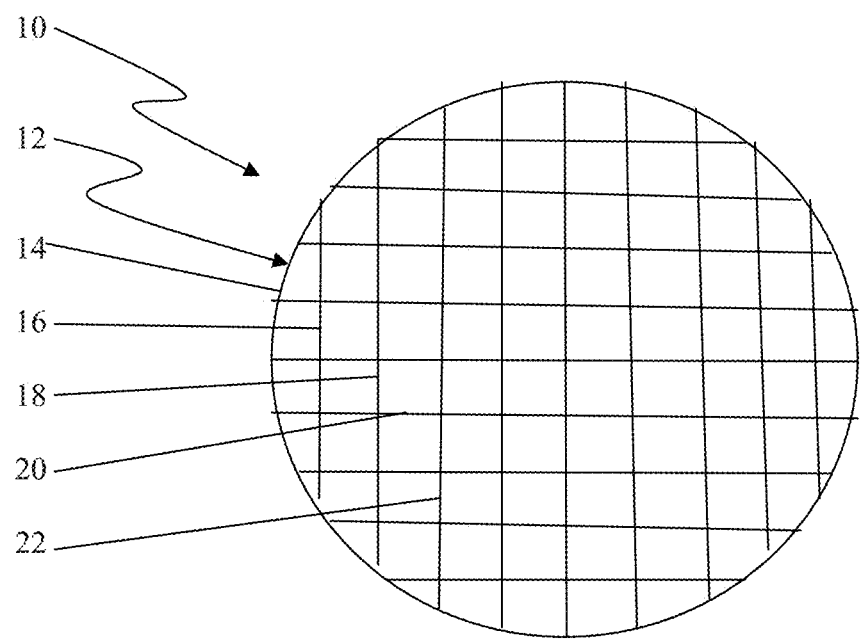
FIG. 1 is a schematic depiction of a meshwork tear shaping structure having an evenly spaced grid pattern according to an example embodiment of the invention.

Referring to FIG. 1, in a schematic depiction, according to an example embodiment of the invention, tear shaping structure 10 may include a lenticular structure 12 having perimeter ring 14 and grid 16 of fibers 18. Perimeter ring 14 supports grid 16 of fibers 18.

In the depicted embodiment, grid 16 of fibers 18 includes horizontal fibers 20 and vertical fibers 22. The adjectives horizontal and vertical are used here for convenience of description and merely to distinguish the substantially perpendicular relative orientation of horizontal fibers 20 from vertical fibers 22. Horizontal fibers 20 and vertical fibers 22 can be in any orientation however they are oriented approximately perpendicular to each other. In the context of the invention approximately perpendicular means within plus or minus 15° of 90°. In the depicted embodiment of FIG. 1 horizontal fibers 20 are substantially evenly spaced from other horizontal fibers 20 that are generally parallel thereto and vertical fibers 22 are substantially evenly spaced from other vertical fibers 22 that are generally parallel thereto. Lenticular structure 12 may be formed as a shell having a shape approximating a portion of the sphere.

Fibers 18 and other structures utilized in tear shaping herein include but are not limited to fibers 18, particles, microscopic particles, nanoparticles, nanostructures or nano robots may be collectively referred to as capillary action structures. This is because the above identified capillary action structures enable the tear film to interact with the capillary action structures to cause shaping of the tear film to support a desired refractive result.

Figure 2:
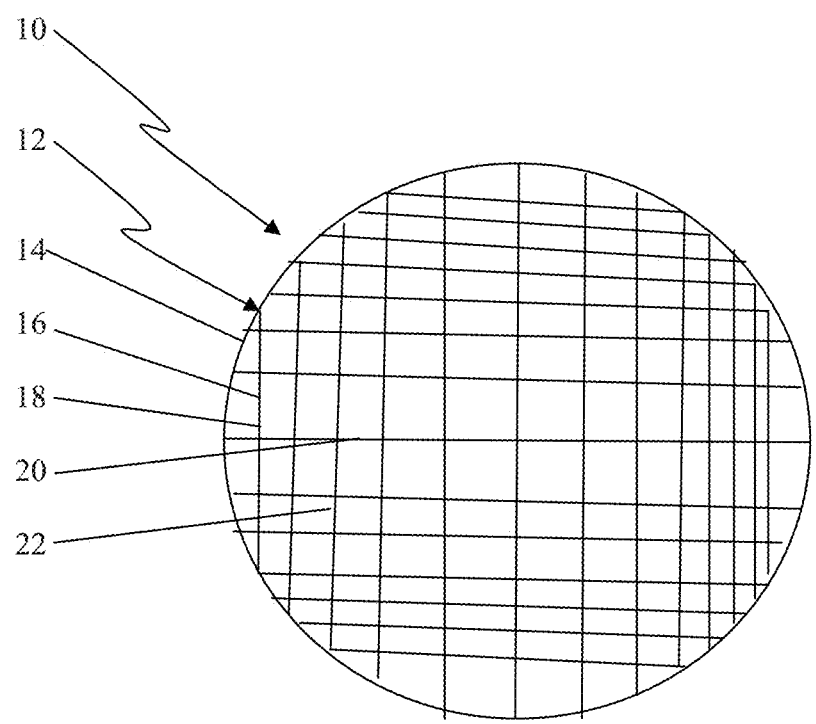
FIG. 2 is a schematic depiction of a meshwork tear shaping structure having a grid pattern more closely spaced peripherally than centrally according to an example embodiment of the invention.

Referring now to FIG. 2, a depicted example embodiment also includes perimeter ring 14 supporting grid 16 of fibers 18 including horizontal fibers 20 and vertical fibers 22. In the depicted embodiment, horizontal fibers 20 and vertical fibers 22 are more distantly spaced centrally and more closely spaced peripherally. In the depicted embodiment, it is expected that such a configuration will result in tear shaping that will focus light to have an overall refractive effect similar to minus power lens to assist in the correction of myopia. While the depicted embodiment includes a similar structure of both horizontal fibers 20 and vertical fibers 22 it is to be understood that, for example, horizontal fibers 20 may be more closely spaced centrally and vertical fibers 22 may be more closely spaced peripherally in which case, it is expected that a mixed astigmatic correction will be achieved. Alternatively, horizontal fibers 20 and vertical fibers 22 may both be space more closely either peripherally or centrally but in varying degrees of spacing.

Figure 3:
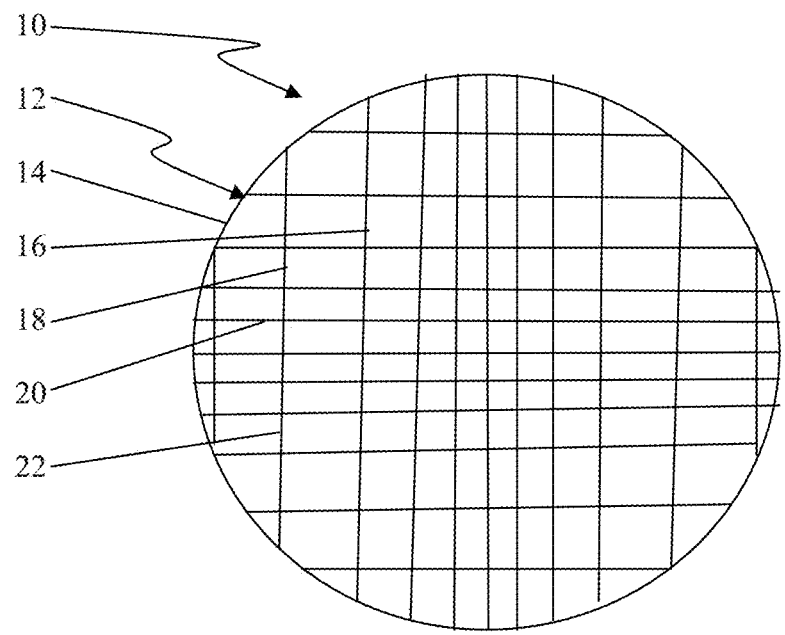
FIG. 3 is a schematic depiction of a meshwork tear shaping structure having a grid pattern more closely spaced centrally than peripherally according to an example embodiment of the invention.

Referring now to FIG. 3, another example embodiment of tear shaping structure 10 is depicted. In the depicted embodiment, horizontal fibers 20 and vertical fibers 22 are more closely spaced a centrally than peripherally. It is expected that such a configuration will provide a tear shape having a focusing effect similar to a plus lens to assist in correcting refractive error for hyperopia. As discussed above, it is to be understood that horizontal fibers 20 and vertical fibers 22 may be differently spaced from each other as to which is spaced closer centrally and which is spaced closer peripherally.

Figure 4:
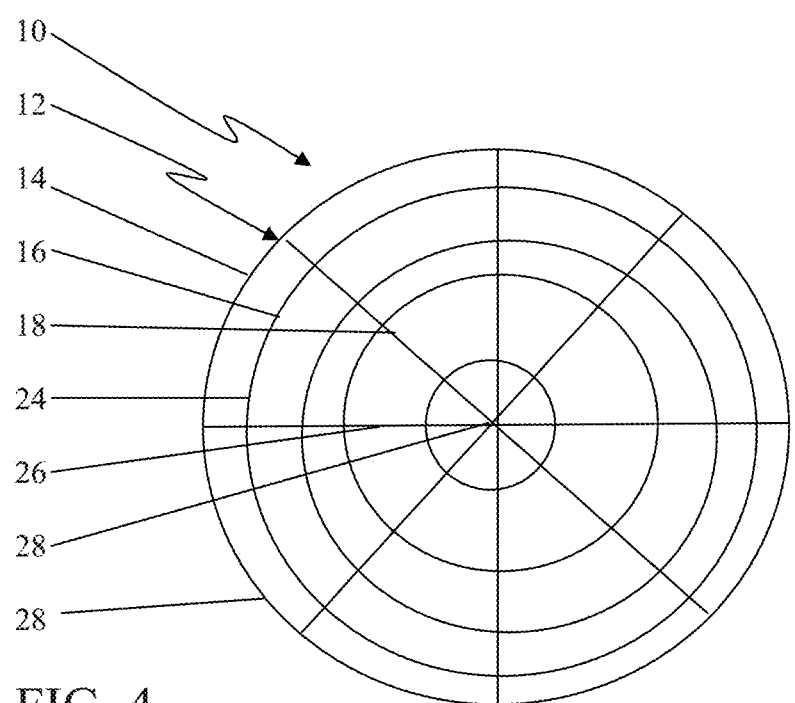
FIG. 4 is a schematic depiction of a meshwork tear shaping structure having meshwork structures oriented radially and circularly and more closely spaced peripherally than centrally according to an example embodiment of the invention.

Referring now to FIG. 4 another schematic example embodiment of tear shaping structure 10 is depicted. The depicted embodiment elliptical fibers 24 and radial fibers 26 are utilized. Elliptical fibers 24 extend generally around a center 28 of tear shaping structure 10. According to example embodiments of the invention, elliptical fibers 24 may follow a circular path or may follow another closed path that includes but is not limited to circular, oval, elliptical or racetrack shaped in nature. In the depicted embodiment, radial fibers 26 extend generally through center 28 and to periphery 30 of tear shaping structure 10. In the depicted embodiment, elliptical fibers 24 are spaced more closely peripherally and more distantly centrally. It is expected that such an arrangement will lead to a negative refractive correction for correcting myopia.

In the context of this application, elliptical fibers 24 are to be understood to include fibers that define a circular path or shape or the other paths or shapes discussed above. It is noted that, from a geometrical standpoint, it is to be understood that a circle is a special case of an ellipse in which the major and minor axis of the ellipse are equal. Thus, elliptical fibers 24 include circular fibers as well.

Figure 5:
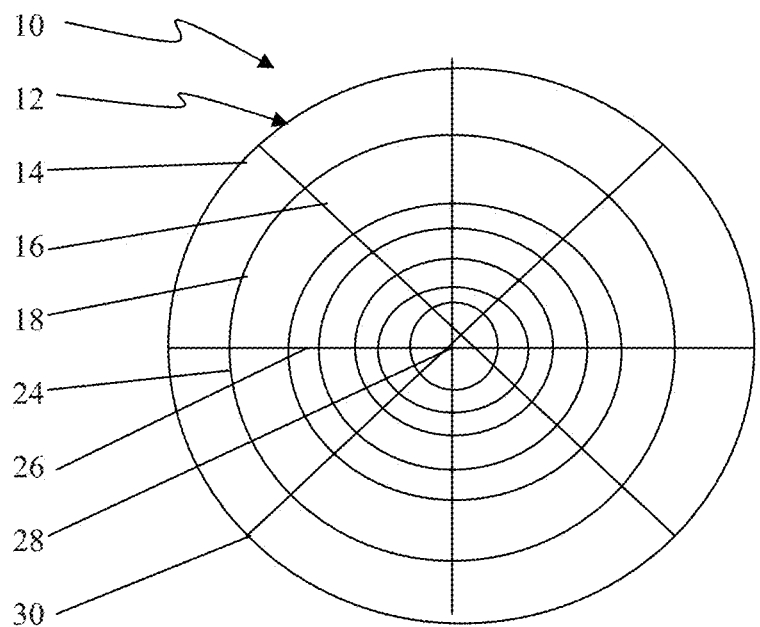
FIG. 5 is a schematic depiction of a meshwork tear shaping structure having meshwork structures oriented radially and circularly and more closely spaced centrally than peripherally according to an example embodiment of the invention.

Referring now to FIG. 5, another example embodiment of tear shaping structure 10 is schematically depicted. This embodiment also includes elliptical fibers 24 and radial fibers 26. In this example embodiment, elliptical fibers 24 are spaced more closely together centrally and more distantly from each other peripherally. Such a configuration is expected to provide a positive refractive correction for correcting myopia.

Figure 6:
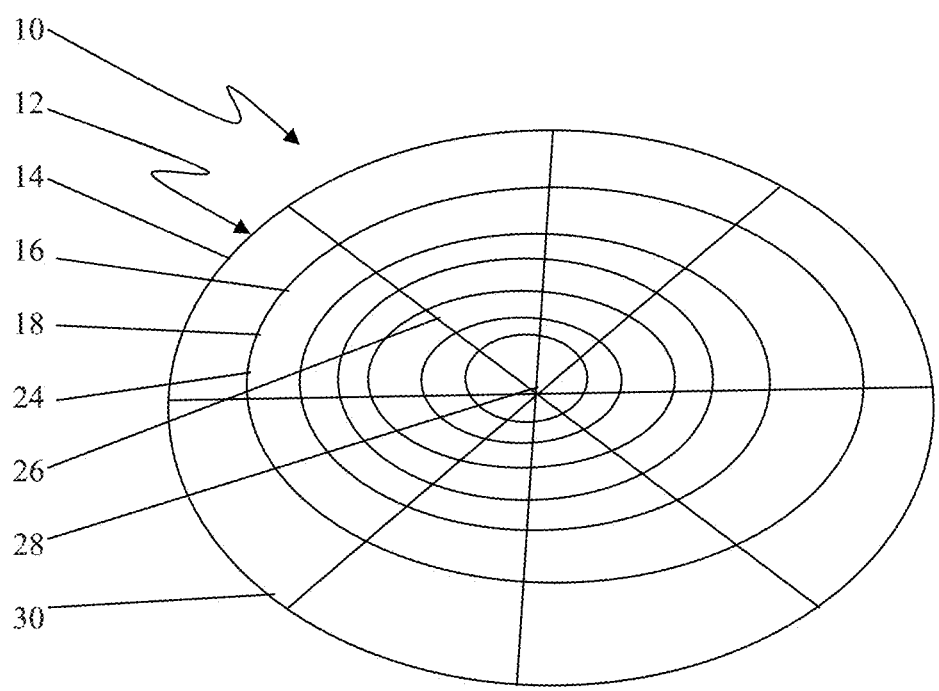
FIG. 6 is a schematic depiction of a meshwork tear shaping structure having meshwork structures oriented radially and elliptically and more closely spaced centrally than peripherally according to an example embodiment of the invention.

Referring now to FIG. 6, another example embodiment of tear shaping structure 10 is schematically depicted. In the depicted embodiment elliptical fibers 24 are elliptically arranged and may be referred to as elliptical fibers 32. In this example embodiment the range of elliptical fibers 32 is more closely spaced centrally and more distantly spaced peripherally. This configuration is expected to provide a refractive correction appropriate for correcting astigmatism.

Figure 7:
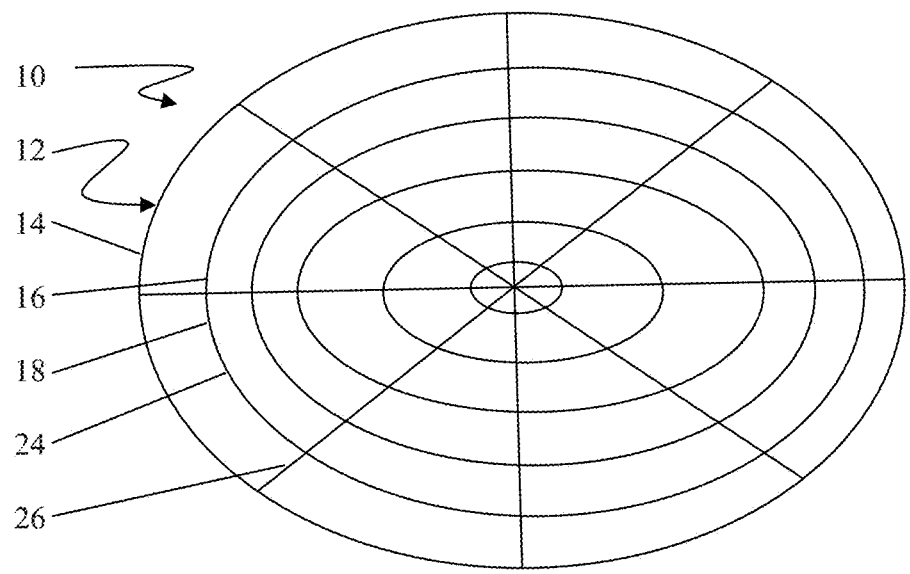
FIG. 7 is a schematic depiction of a meshwork tear shaping structure having meshwork structures oriented radially and elliptically and more closely spaced peripherally than centrally according to an example embodiment of the invention.

Referring to FIG. 7, another example embodiment of tear shaping structure 10 is schematically depicted. In this example embodiment, elliptical fibers 32 are present and spaced more closely peripherally than they are centrally. In addition radial fibers 26 are present and spaced more closely angularly in some orientations than other orientations. The depicted arrangement is expected to assist in providing refractive correction for astigmatism.

Figure 8:
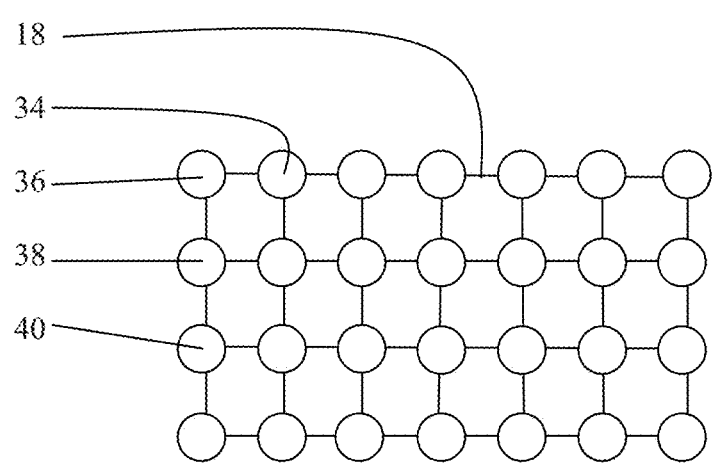
FIG. 8 is a schematic depiction of a meshwork tear shaping structure having additional structural components at junctions of fibers.

Referring to FIG. 8, a schematic depiction of a grid structure of a tear shaping structure 10 is depicted having additional structural components at junctions 34 of fibers 18. As depicted here, fibers 18 includes horizontal fibers 20 and vertical fibers 22. Junctions 34 include additional spherical structures 36. Embodiments of the invention are not, however, limited to spherical structures 36. Similar structures may be present in other shapes such as cubes, tetrahedra, octahedra or other polyhedral shapes including for example, the five Platonic solids. Other three-dimensional structures may be utilized as well. In addition, spherical structures 36 may also be located at junctions of elliptical fibers 24 and radial fibers 26.

According to other example embodiments of the invention, some of fibers 18 may be formed to be thicker or thinner than other of fibers 18. Variations in fiber 18 thickness are expected to provide a different refractive correction or prismatic correction. According to another example embodiment of the invention fibers 18 may vary in cross sectional shape to assist in shaping the tear film. Cross-sectional shapes may include but are not limited to circular, polygonal, triangular, dentate or irregular shapes.

According to another example embodiment of the invention, tear shaping structure 10 may be formed by perforating a solid structure with a multitude of openings. According to example embodiments of the invention, the openings may be circular, square, rectangular, polygonal or of any other shape.

According to another example embodiment of the invention, perimeter ring 14 may surround a periphery of tear shaping structure 10. Perimeter ring 14 may be formed of similar material to the rest of tear shaping structure 10 or may be formed of an alternative material, for example, a material of greater rigidity than the rest of tear shaping structure 10.

According to another example embodiment of the invention, additional surface features 38 may include textured features 40. Surface features 38 including textured features 40 may present nodules or indentations of a microscopic or nano structural size level in order to further assist in shaping the tear film as desired.

Tear shaping structure 10 may be formed of a durable material or may be formed of a bioabsorbable or biodegradable material. According to one example embodiment tear shaping structure 10 may be formed of collagen.

Figure 9:
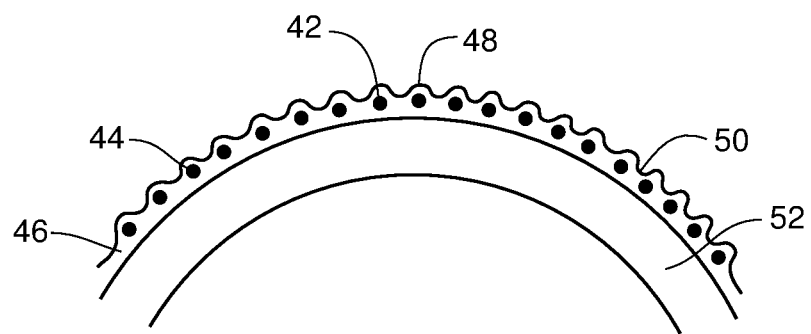
FIG. 9 is a schematic depiction of a tear shaping formation including a large number individual structural components instilled in a tear film according to an example embodiment of the invention.

Referring to FIG. 9 tear shaping structure 10 may include independent tear shaping objects 42. Independent tear shaping objects 42 may include micro-balloons, microspheres, micro rings, irregular shaped objects or a combination of the foregoing. Independent tear shaping objects 42 may vary in size.

As depicted in FIG. 9 tear shaping objects 42 may include microspheres 44. As depicted in FIG. 9, microspheres 44 are dispersed relatively evenly in tear film 46. The presence of tear shaping objects 42 such as microspheres 44 is expected to cause tear film 46 to present convex areas 48 and concave areas 50. Depending upon the size, shape and spacing of tear shaping objects 42 is expected that either convex areas 48 or concave areas 50 will dominate and contribute to a positive refractive correction or a negative refractive correction. A positive refractive correction is expected to occur if convex areas 48 dominate. A negative refractive correction is expected to occur if concave areas 50 dominate. Tear film 46 and tear shaping objects 42 are depicted overlying cornea 52.

Figure 10:
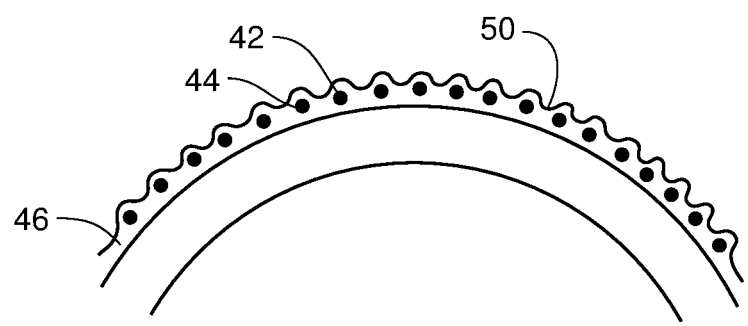
FIG. 10 is a schematic depiction of a tear shaping formation including a large number individual structural components that are cylindrical or of another shape instilled in a tear film according to an example embodiment of the invention.

Referring now to FIG. 10, an example embodiment of the invention is depicted in which concave areas 50 indirectly created dominate thus a negative refractive effect is expected.

Figure 11:
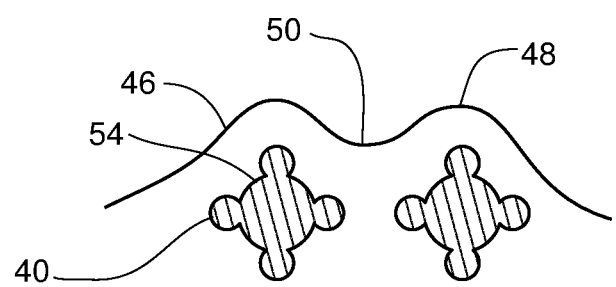
FIG. 11 is a schematic depiction of a tear shaping formation including a large number of multi-lobate individual structural components instilled in the tear film according to a further example embodiment of the invention.

Referring to FIG. 11, tear shaping objects 42 may include irregular shapes such as multi-lobate tear shaping object 54. Multi-lobate tear shaping object 54 are expected to enable control distance between tear shaping objects 42 thus assisting in control of the tear film shaping.

Figure 12:
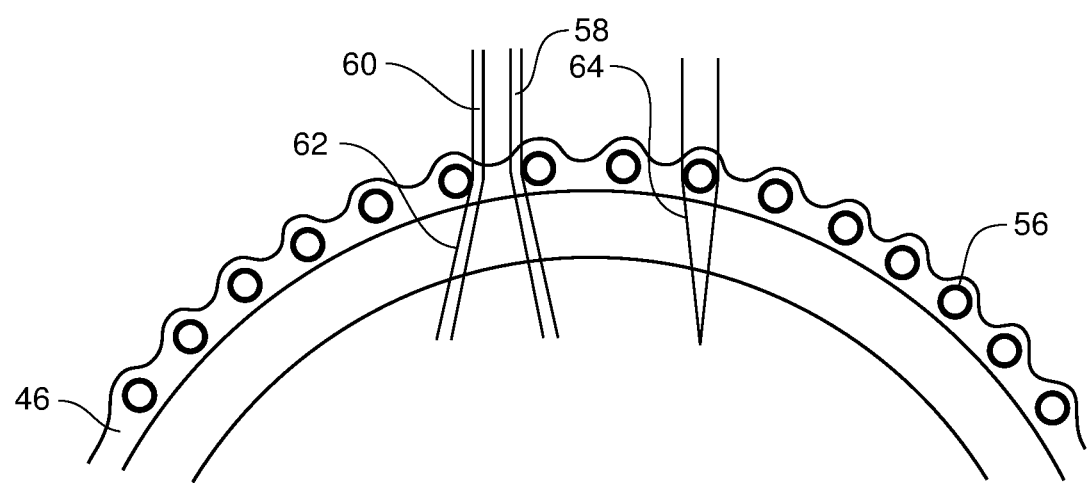
FIG. 12 is a schematic depiction of a tear shaping formation including a large number of individual structural components that are ring-shaped or hollow cylindrical shaped instilled in the tear film according to a further example embodiment of the invention While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

Referring to FIG. 12, tear shaping micro rings 56 are depicted. Micro rings 56 include ring-shaped or cylinder shaped objects having an open center. Depending upon the size of micro rings 56 it is expected that positive refractive effects or negative refractive effects may be achieved. Tear shaping micro rings 56 may include circular, elliptical, oval and/or racetrack shaped rings. Micro rings 56 may have a ring a portion that is the same size around its entire circumference or a ring-shaped portion that varies in size around the circumference.

FIG. 12 also includes a depiction of light rays 58 impinging upon tear film 46 in convex areas 48 and concave areas 50. Parallel light rays 60 impinging upon concave areas 50 are diverged which is expected to lead to a minus lens effect by creating diverging light rays 62. Parallel right light rays 60 impinging upon convex areas 48 are converged which is expected to lead to a plus lens effect by creating converging light rays 64.

According to another example embodiment of the invention, independent tear shaping objects 42 may be positioned relative to one another by attractive and repulsive forces.

According to another example embodiment of the invention, independent tear shaping objects 42 may be applied dispersed in a liquid suspension which is instilled into the tears such that individual structural members may position themselves relative to one another by attractive and repulsive forces once introduced into the tear film. Independent tear shaping objects 42 may be supported in a sol or gel suspension. Independent tear shaping objects 42 may also be partially cross-linked or interlinked while in the suspension and further organized once instilled into the tear film.

Independent tear shaping objects 42, according to an example embodiment of the invention, may be organized by capillary action in combination with electrostatic forces, magnetic forces, intermolecular forces, and/or various repulsive and/or attractive forces. According to example embodiments of the invention Independent tear shaping objects 42 may vary in size and configuration. A suspension may include independent tear shaping objects 42 of a single size and configuration or of several sizes and configurations. According to example embodiments of the invention, independent tear shaping objects 42 may be organized to provide correction for myopia, presbyopia, hyperopia, astigmatism, and prismatic correction.

According to example embodiments of the invention, independent tear shaping objects 42 may include microscopic structural members, nanostructural members or even nano-robots.

According to another example embodiment, independent tear shaping objects 42 may be configured to provide correction for myopia, hyperopia, astigmatism, presbyopia and other refractive errors. According to another example embodiment, capillary action structures, meshwork structural members or independent tear shaping objects 42 may be configured to improve image quality by reducing higher-order aberrations or spherical aberration of the eye or by providing compensation for corneal irregularities that exist due to disease or injury.

In operation, tear shaping structure 10 is applied to an eye. In the case of lenticular structure 12, lenticular structure 12 is applied to the eye in a way that is similar to application of a contact lens. Grid 16 of fibers 18 interacts with the tear film in such a way that the tear film occupies the space between horizontal fibers 20, vertical fibers 22, elliptical fibers 24 and/or radial fibers 26 because of capillary action. Capillary action causes the tear film to be shaped such that it has a changed refractive effect from the unshaped tear film. Thus, fibers 18 contribute to shaping of the tear film such that the tear film does not create a smooth layer over the corneal surface and instead alters the refractive interface between the tear film and the atmosphere to create a desired refractive effect to compensate for ametropia.

In the case of uneven spacing of fibers 18, refractive effects are expected to include compensation for astigmatism and/or compensation for prismatic effects. Varying spacing of elliptical fibers 24 and/or radial fibers 26 also are expected to provide refractive compensation for astigmatism.

In the case of independent tear shaping objects 42, these structures may be introduced into the eye in a liquid suspension or a sol/gel suspension. Independent tear shaping objects 42 are expected to organize themselves because of attractive and repulsive forces to alter the tear film to provide refractive benefits.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A shaping structure to shape a tear film of an eye, comprising:
   a supporting structure having a plurality of independent and separate liquid shaping capillary action structures that are structured to interact with a liquid film by capillary action, the liquid shaping capillary action structures being spaced apart thereby defining a plurality of independent and separate circumscribed passages therebetween, the plurality of independent and separate circumscribed passages each being surrounded by and circumferentially enclosed by the liquid shaping capillary action structures whereby fluid communication through each of the passages of the shaping structure exists and the liquid shaping capillary action structures being arranged in such a way as to create a desired refractive lens effect by shaping the liquid film proximate each of the plurality of independent and separate passages when the liquid shaping capillary action structures are immersed in the tear film.

2. The tear shaping structure as claimed in claim 1, wherein the liquid shaping capillary action structures comprise a plurality of fibers or filaments arranged in a grid structure.

3. The tear shaping structure as claimed in claim 2, wherein the grid structure includes mutually substantially perpendicular fibers or filaments in a first orientation and a second orientation and wherein the fibers or filaments in at least one orientation are evenly spaced apart from each other in at least one meridian.

4. The tear shaping structure as claimed in claim 2, wherein the grid structure includes mutually substantially perpendicular fibers or filaments in a first orientation and a second orientation and wherein the fibers or filaments in at least one of the first and second orientation are spaced apart from each other at a greater distance centrally than peripherally in at least one meridian.

5. The tear shaping structure as claimed in claim 2, wherein the grid structure includes mutually substantially perpendicular fibers or filaments in a first orientation and a second orientation and wherein the fibers or filaments in at least one of the first and second orientation are spaced apart from each other at a greater distance centrally than peripherally in at least one meridian.

6. The tear shaping structure as claimed in claim 1, wherein the liquid shaping capillary action structures further comprise a plurality of fibers or filaments including radial fibers or filaments arranged in a radial orientation and elliptical fibers or filaments arranged in an elliptical orientation.

7. The tear shaping structure as claimed in claim 6, wherein the elliptical fibers or filaments are spaced apart from each other more closely centrally and more distantly peripherally.

8. The tear shaping structure as claimed in claim 6, wherein the elliptical fibers or filaments are spaced apart from each other more closely peripherally and more distantly centrally.

9. The tear shaping structure as claimed in claim 6, wherein the radial fibers or filaments are angularly spaced apart from each other more closely in some meridional orientations than in other meridional orientations.

10. The tear shaping structure as claimed in claim 6, wherein the elliptical fibers or filaments further circumscribe a circular path, an elliptical path, an oval path or a race track shaped path.

11. The tear shaping structure as claimed in claim 2, further comprising additional three-dimensional structural components at junctures of crossing fibers or crossing filaments.

12. The tear shaping structure as claimed in claim 2, wherein a first subset of the fibers or filaments has a first cross sectional diameter and a second subset of fibers or filaments has a second cross sectional diameter.

13. The tear shaping structure as claimed in claim 2, wherein a first subset of the fibers or filaments has a first cross sectional shape and a second subset of fibers or filaments has a second cross sectional shape.

* * * * *